United States Patent
Shin

(10) Patent No.: US 9,320,624 B2
(45) Date of Patent: Apr. 26, 2016

(54) METHOD FOR MANUFACTURING A STENT HAVING SUPERIOR BENDING CHARACTERISTICS, AND STENT MANUFACTURED THEREBY

(75) Inventor: Kyong Min Shin, Seoul (KR)

(73) Assignees: TAEWOONG MEDICAL Co., LTD., Gyeonggi-do (KR); Kyong Min Shin, Seoul (KR)

(*) Notice: Subject to any disclaimer, the term of this patent is extended or adjusted under 35 U.S.C. 154(b) by 267 days.

(21) Appl. No.: 13/978,020

(22) PCT Filed: Jan. 10, 2012

(86) PCT No.: PCT/KR2012/000238
§ 371 (c)(1),
(2), (4) Date: Jul. 2, 2013

(87) PCT Pub. No.: WO2012/096497
PCT Pub. Date: Jul. 19, 2012

(65) Prior Publication Data
US 2013/0282105 A1    Oct. 24, 2013

(30) Foreign Application Priority Data
Jan. 14, 2011  (KR) ................. 10-2011-0004078

(51) Int. Cl.
*A61F 2/90* (2013.01)
*B21F 27/12* (2006.01)
*B21F 45/00* (2006.01)

(52) U.S. Cl.
CPC ............. *A61F 2/90* (2013.01); *B21F 27/121* (2013.01); *B21F 45/008* (2013.01); *A61F 2240/00* (2013.01)

(58) Field of Classification Search
CPC ................ A61F 2/06; A61F 2/82; A61F 2/90
USPC ................................ 623/1.15–1.54
See application file for complete search history.

(56) References Cited

U.S. PATENT DOCUMENTS

| 6,063,113 A | * | 5/2000 | Kavteladze | A61B 17/0057 606/200 |
| 7,462,192 B2 | * | 12/2008 | Norton | A61F 2/90 264/103 |
| 8,869,670 B1 | * | 10/2014 | Janardhan | A61F 2/01 623/1.53 |
| 2005/0096733 A1 | * | 5/2005 | Kovneristy | A61F 2/90 623/1.22 |

(Continued)

FOREIGN PATENT DOCUMENTS

| JP | 2003-088591 | 3/2003 |
| KR | 100424290 | 3/2004 |

(Continued)

*Primary Examiner* — Suzette J Gherbi
(74) *Attorney, Agent, or Firm* — IP & T Group LLP

(57) ABSTRACT

Provided is a method for manufacturing a stent having a superior bending characteristic, in which a basic jig is employed to weave wires by alternating an obtuse angle and an acute angle so as to repetitively form starry cells in left and right portions and upper and lower portions of the stent, and in which the wires intersecting each other in the starry cells are allowed to freely move to provide the superior bending characteristic caused by flexibility in both the diametrical direction and lengthwise direction thereof, and the stent manufactured thereby. Thus, the stent can have a flexible bending characteristic and is prevented from being folded even when sharply bent after being coated.

4 Claims, 20 Drawing Sheets

(56) References Cited

U.S. PATENT DOCUMENTS

| | | | |
|---|---|---|---|
| 2009/0306762 A1* | 12/2009 | McCullagh | A61F 2/90 623/1.13 |
| 2011/0029062 A1* | 2/2011 | Kang | A61F 2/07 623/1.15 |
| 2011/0144739 A1* | 6/2011 | Cattaneo | A61F 2/88 623/1.22 |
| 2014/0088688 A1* | 3/2014 | Lilburn | D04C 1/06 623/1.15 |
| 2015/0045874 A1* | 2/2015 | McMahon | A61F 2/88 623/1.22 |

FOREIGN PATENT DOCUMENTS

| | | |
|---|---|---|
| KR | 100457629 | 11/2004 |
| KR | 100826664 | 5/2008 |
| KR | 1020090038209 | 4/2009 |
| KR | 1020100042478 | 4/2010 |

* cited by examiner

METHOD FOR MANUFACTURING A STENT HAVING SUPERIOR BENDING CHARACTERISTICS, AND STENT MANUFACTURED THEREBY

This application is a national stage application of PCT/KR2012/000238 filed on Jan. 10, 2012, which claims priority of Korean patent application number 10-2011-0004078 filed on Jan. 14, 2011. The disclosure of each of the foregoing applications is incorporated herein by reference in its entirety.

TECHNICAL FIELD

The present invention relates, in general, to a stent, and more particularly, to a method for manufacturing a stent having a superior bending characteristic, in which the stent is flexibly bent and is prevented from being folded even when sharply bent, and a wire constituting the stent provides a superior bending characteristic and is prevented from being twisted after being coated, and the stent manufactured thereby.

BACKGROUND ART

To dilate internal organs such as a bile duct which are being narrowed or are narrowed by a tumor formed by growth of cancer cells in the villus or its surroundings of the internal organs, medical stents are used.

Various conventional medical stents having various structures are known. As shown in FIG. 1, such a stent is manufactured by weaving a wire 1 formed of a superelastic shape memory alloy or stainless steel so as to be crossed at different positions and by forming a hollow cylindrical body 3 having a plurality of rhombic spaces (cells) 2 and a predetermined length.

To prevent cells growing at a spot where a procedure is to be performed, i.e. cancer cells, from penetrating into the stent, the interior and exterior of the cylindrical body 3 are coated with polytetrafluoroethylene (PTFE) or silicone that is not harmful to a human body.

This stent is manufactured as shown in FIG. 2 by bending and crossing the wire 1 formed of a superelastic shape memory alloy or stainless steel in directions perpendicular to circumferential and lengthwise directions using a basic jig 10 in which a plurality of projecting pins 11 are uniformly assembled in the circumferential and lengthwise directions so as to have a preset diameter Ø and length L, and by forming the rhombic cells 2 so as to be expanded/contracted at intersections in diametrical and lengthwise directions. The stent has an elastic force in the diametrical and lengthwise directions so as to be restored in its original state of a cylindrical shape formed by the basic jig 10 as long as the stent is not forcibly pressed by an external force.

The stent manufactured using this basic jig 10 is disclosed in Korean Unexamined Patent Application Publication Nos. 10-2001-18024 and 10-2001-18026, both of which are the prior applications of the applicant of the present invention.

DISCLOSURE

Technical Problem

The conventional stent is manufactured such that the wire for forming the cells is bent in a right-angled direction. There is no great difficulty in using the stent in a narrowed, smoothly curved blood vessel of the human body. However, when the blood vessel into which the stent is inserted is sharply curved, the stent has a disadvantage in that it fails to provide a flexible bending characteristic so as to correspond to curvature.

Furthermore, in the case of a coated structure for blocking cell penetrable spaces formed by the weaving of the wire formed of a superelastic shape memory alloy or stainless steel, the bending characteristic is further degraded, and thus the stent exhibits a poor bending characteristic when used in vessels with sharply curved portions.

Accordingly, the present invention has been made keeping in mind the above problems occurring in the related art, and is intended to provide a method for manufacturing a stent having a superior bending characteristic, in which wires are woven by alternating an obtuse angle and an acute angle so as to repetitively form starry cells in left and right portions and upper and lower portions of the stent, and in which the wires intersecting each other in the starry cells are allowed to freely move to provide the superior bending characteristic caused by flexibility in both the diametrical direction and lengthwise direction thereof, and the stent manufactured thereby.

Technical Solution

In an aspect, the present invention provides a method of manufacturing a stent having a superior bending characteristic, in which a basic jig is used in which projecting pins are assembled at all transition points at which circumference dividing lines and length dividing lines set by equally dividing a circumference and length of a cylinder having the same diameter and length as the stent to be manufactured cross one another, includes a downward wire bending process of moving a strand of wire, which has a predetermined length and is formed of a superelastic shape memory alloy or stainless steel, from an upper starting point to a transition point (projecting pin) at a four-segment diagonal distance to which an upper head is formed in a downward direction and in lengthwise and circumferential directions, bending and moving the wire three times a one-segment diagonal distance at an acute angle and three times a two-segment diagonal distance at an obtuse angle from the transition point (reference point) to another transition point in a zigzag pattern in the lengthwise and circumferential directions, and repeating this process to move the wire at a predetermined distance in the downward direction;

a lower head forming process of bending and moving the wire from the transition point located in the downward wire bending process five times the one-segment diagonal distance at the acute angle in the lengthwise and circumferential directions again, bending and moving the wire from the transition point to another transition point two times a four-segment diagonal distance in a zigzag pattern in the lengthwise and circumferential directions, bending and moving the wire from the transition point to another transition point six times the four-segment diagonal distance in a zigzag pattern in the lengthwise and circumferential directions, and forming a lower head having sexangular bending finishing ends;

an upward wire bending process of bending and moving the wire from the transition point located in the lower head forming process to another transition point seven times the one-segment diagonal distance in the zigzag pattern in the lengthwise and circumferential directions again, bending and moving the wire from the transition point to another transition point three times the two-segment diagonal distance in the zigzag pattern in the lengthwise and circumferential directions, bending and moving the wire from the transition point to another transition point two times the one-segment diagonal distance in the zigzag pattern in the lengthwise and circumferential directions, bending and moving the wire six times from the transition point to another transition point six times the two-segment diagonal distance in the lengthwise and circumferential directions, bending and moving the wire from the transition point to another transition point seven times the one-segment diagonal distance in the zigzag pattern in the lengthwise and circumferential directions, and repeating this process to bend and move the wire at a predetermined distance in the upward direction, whereby the wires are joined crosswise at the transition points (bending vertexes) overlapped with the transition points of the downward wire bending process, and are bent in the upward direction;

an upper head forming process of bending and moving the wire from the transition point located in the upward wire bending process to another transition point two times the one-segment diagonal distance at the acute angle in the zigzag pattern in the lengthwise and circumferential directions again, bending and moving the wire from the transition point to another transition point six times the four-segment diagonal distance in the zigzag pattern in the lengthwise and circumferential directions, bending and moving the wire from the transition point to another transition point two times the one-segment diagonal distance at the acute angle in the zigzag pattern in the lengthwise and circumferential directions, bending and moving the wire from the transition point to another transition point six times the four-segment diagonal distance in the zigzag pattern in the lengthwise and circumferential directions, and forming an upper head having the sexangular bending finishing ends; and a finishing connecting process of bending and moving the wire from the transition point located in the upward wire bending process to another transition point (projecting pin) three times the one-segment diagonal distance at the acute angle in the zigzag pattern in the lengthwise and circumferential directions, positioning the wire at the two-segment diagonal distance at the obtuse angle in the lengthwise and circumferential directions once, and connecting the portion overlapped with the wire bent and positioned in the downward wire bending process by welding.

The stent manufactured by this manufacturing method is configured so that the cells formed by the crossed wires are formed as repetitive starry cells in which the acute angle bending vertexes bent at the acute angle and the obtuse angle bending vertexes bent at the obtuse angle are joined crosswise and in which the obtuse angle bending vertexes bent at the obtuse angle and the acute angle bending vertexes bent at the acute angle are crossed, and so that the wire bent at the obtuse angle are formed in the starry cell in a simple crossed structure, and provides a flexible bending characteristic by expansion/contraction between the bent vortexes joined crosswise in the event of expansion/contraction or bending in a lengthwise direction and simultaneously by rapid movement of the internal crossed wires.

Advantageous Effects

According to the present invention, a strand of wire is bent from an upper portion to a lower portion at acute and obtuse angles, and from the lower portion to the upper portion at the acute and obtuse angles again. In this process, the bent wire is joined crosswise with another bent wire at bent vortexes, and moves upward. The wires are crossed in opposite directions at the bent vortexes, thereby repetitively forming starry cells. As a result, a stent having a predetermined size is rapidly manufactured.

The cells formed at the wire intersections have a unique starry shape without being folded when expanded/contracted and bent. Thereby, the stent is flexibly bent without being folded after being coated, and thus reliability of a product is ensured.

LIST OF SYMBOLS USED FOR MAIN PARTS OF THE DRAWINGS

10: basic jig, 11: projecting pin, 100: stent, 200: wire, 201: acute angle bending vertex, 202: obtuse angle bending vertex, 210, 211: bending finishing end, 300: welding, C1: rhombic cell, C2: starry cell Best Mode The present invention provides a stent that has a superior bending characteristic, is flexibly bent, and is prevented from being folded even when sharply bent, and includes a wire that provides a superior bending characteristic and is prevented from being twisted after being coated.

Mode for Invention

The characteristic primary gist of the present invention can be specified as ensuring a bending characteristic of a stent and providing a flexible bending characteristic after the stent is coated, preventing the stent from folded even when it is bent sharply.

Hereinafter, exemplary embodiments of the present invention will be described in detail with reference to the accompanying drawings.

Figure 1:
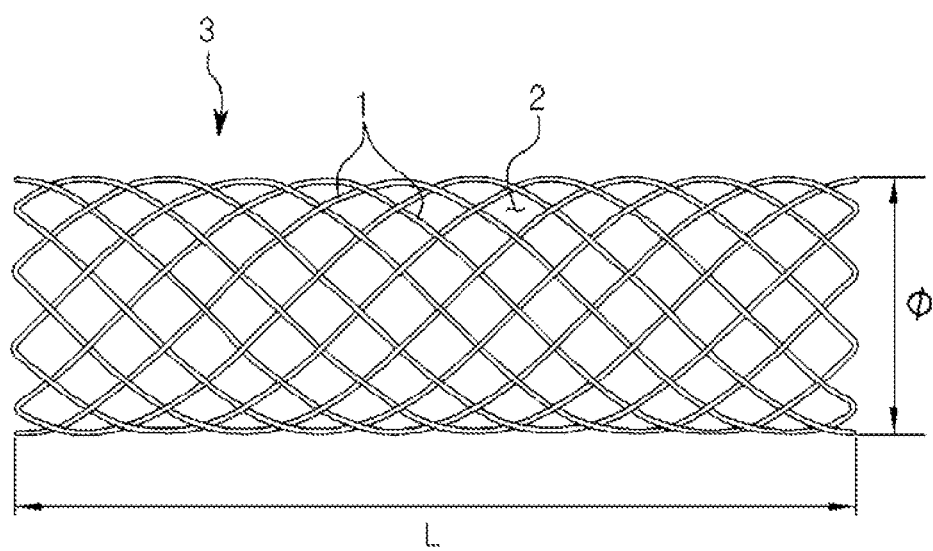
FIG. 1 is a front configuration view of a conventional stent.
Figure 2:
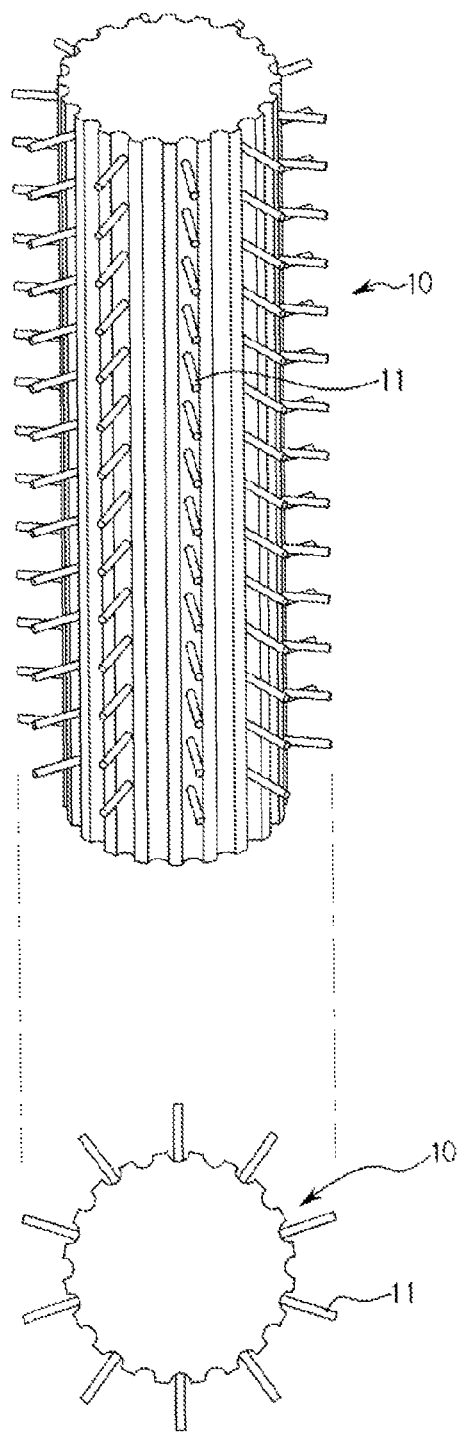
FIG. 2 is a perspective view and a plan view of a basic jig used to manufacture the stent.
Figure 3:
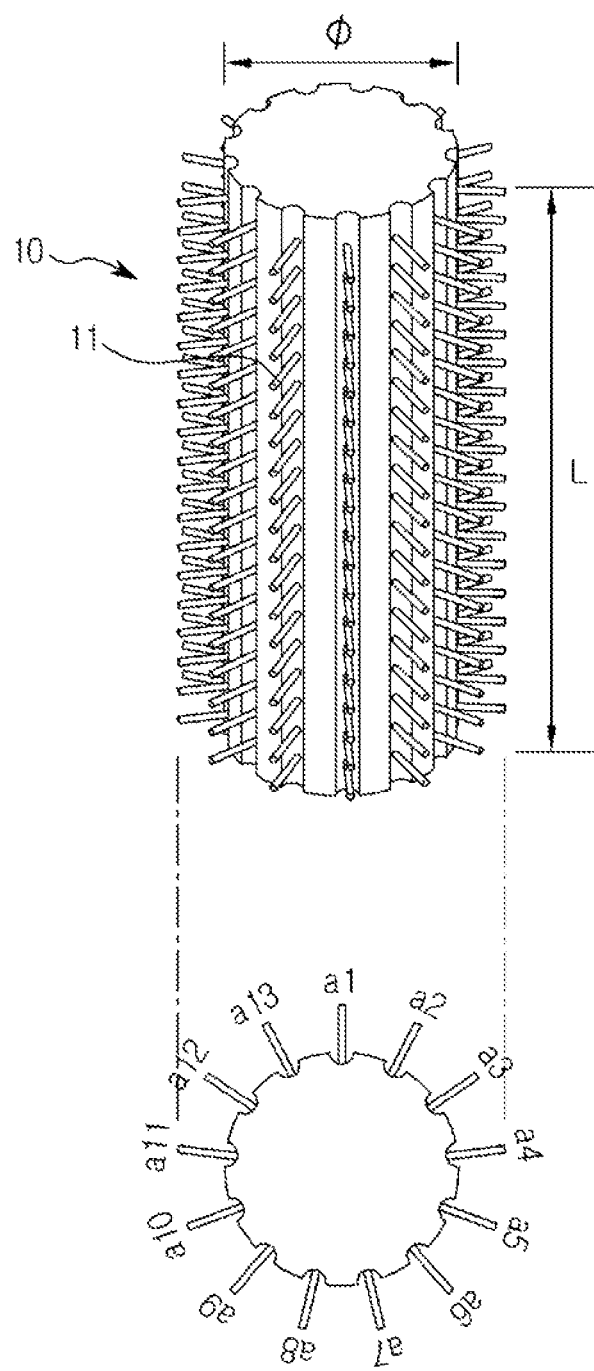
FIG. 3 is a perspective view and a plan view of a basic jig applied to the present invention.

In FIG. 3, a basic jig applied to carry out the present invention is shown.

This basic jig 10 is used in which projecting pins 11 are assembled at all transition points at which circumference dividing lines a1, a2, a3, ..., a13 and length dividing lines b1, b2, b3, ..., b17, which are set by equally dividing a circumference W and length L of a cylinder having the same diameter Ø and length L of a stent to be manufactured, cross one another.

A detailed configuration of the basic jig is disclosed in Korean Unexamined Patent Application Publication Nos. 10-2001-18024 and 10-2001-18026, both of which are the prior applications of the applicant of the present invention. The basic jig 10 applied to the present invention is different in that the numbers of circumference dividing lines a1, a2, a3, . . . , a13 and length dividing lines b1, b2, b3, . . . , b17, which are set by equally dividing the circumference-to-diameter ratio W and the length L are increased.

A manufacturing method of the present invention using the basic jig 10 will be described.

The manufacturing method of the present invention includes a downward wire bending process, a lower head forming process, an upward wire bending process, an upper head forming process, and a finishing connecting process of connecting a start end and a terminal end of a wire.

Further, the present invention manufactures a stent 100 using a strand of superelastic shape-memory-alloy or stainless wire (hereinafter referred to as a "wire") having given standards per centimeter.

First, any one of the circumference dividing lines a1, a2, a3, . . . , a13 of the basic jig 10 is set as an arbitrary reference point a1, and a wire 200 extends from the reference point a1 to the projecting pin 11 located at a transition point a5/b2 that is spaced apart from the reference point by a four-segment diagonal distance (4 l) set in the resultant direction of the length L and the diameter Ø.

This process is a basic process of carrying out the upper head forming process.

Here, a one-segment length by which the wire 200 moves along a diagonal line of the length L and the diameter Ø can be defined as a one-segment diagonal distance (1 l). It is appropriate to understand that, in the following description, the transition point is a point at which the wire is bent at each projecting pin 11 assembled into the basic jig 10.

Figure 4:
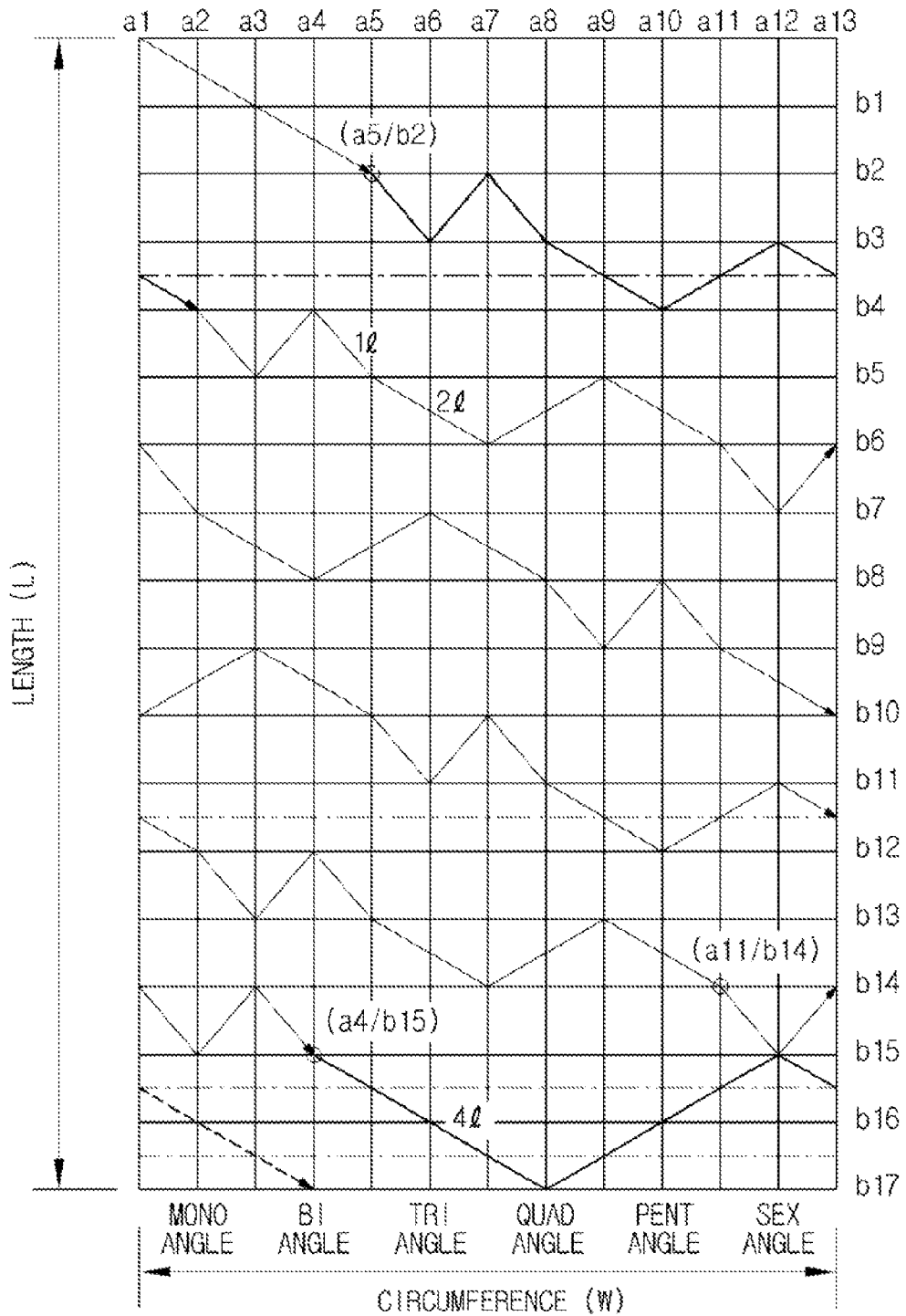
FIGS. 4 and 5 are development views for describing a downward wire bending process of the present invention.

As shown in FIG. 4, the wire travels three times the one-segment diagonal distance (1 l) from the transition point a5/b2 of the four-segment diagonal distance (4 l) to a transition point a8/b3 in a zigzag pattern at an acute angle, and then travels three times the two-segment diagonal distance (2 l) from the transition point a8/b3 to a transition point a2/b4 in a zigzag pattern at an obtuse angle.

Figure 5:
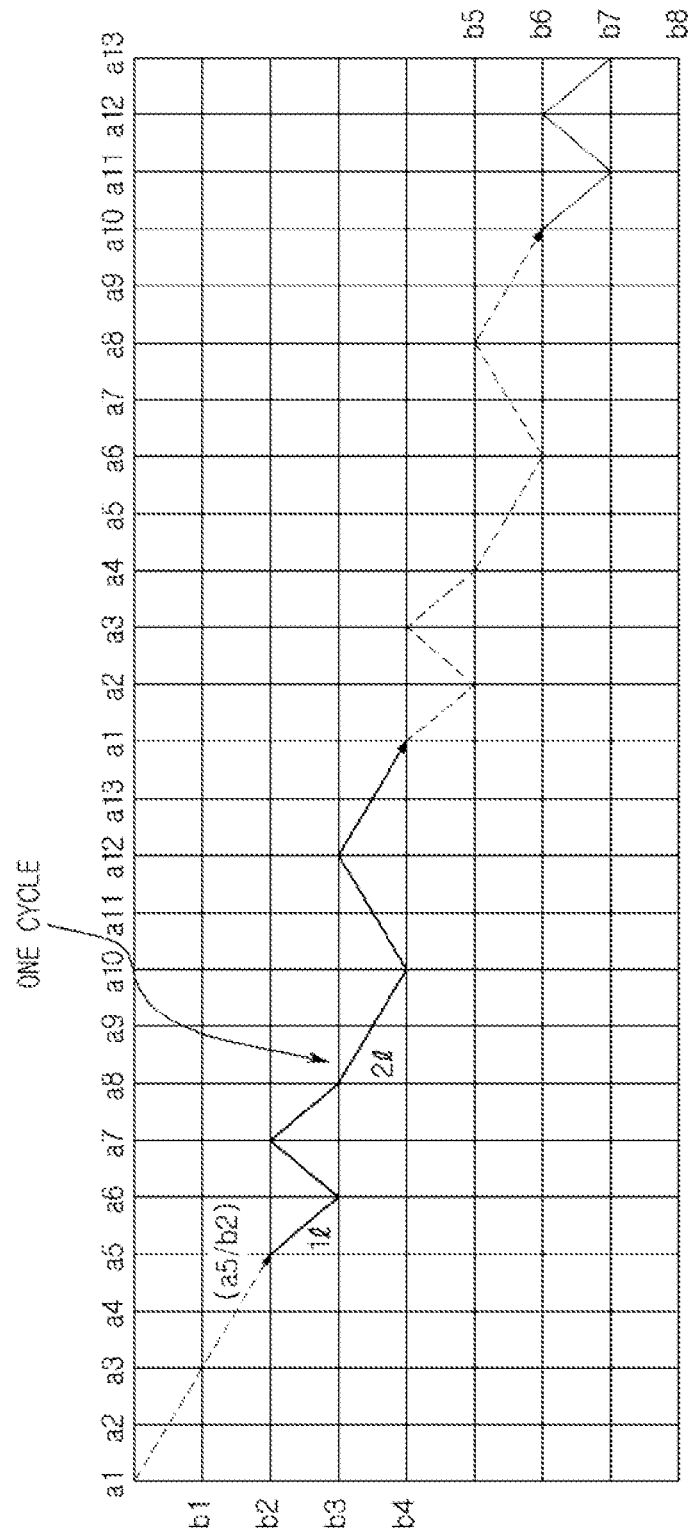
Figure 6:
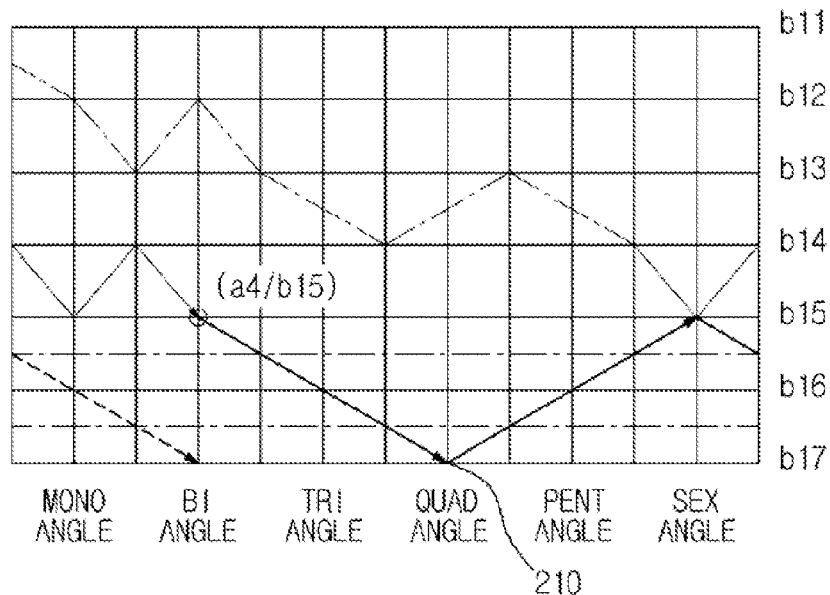
FIGS. 6 to 9 are development views for describing a lower head forming process of the present invention.
Figure 7:
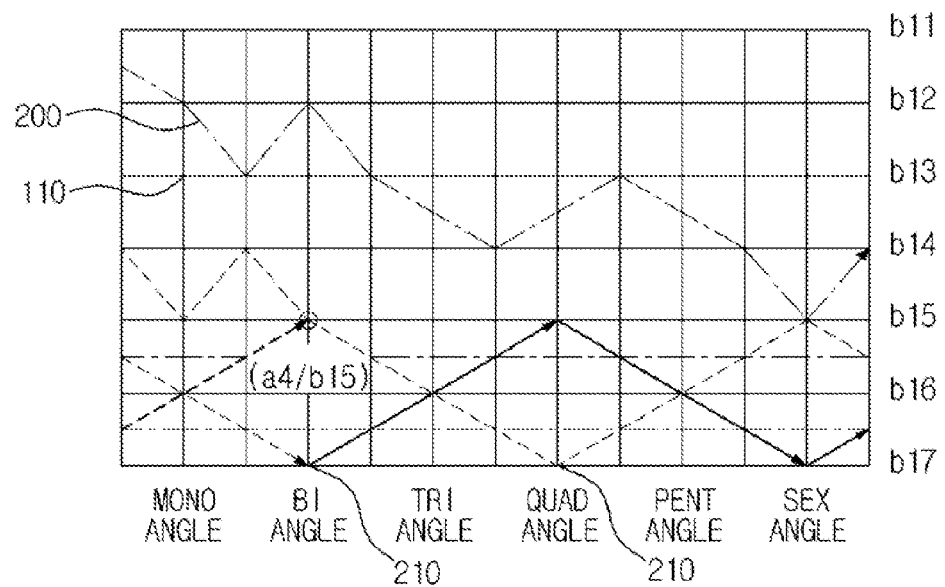
Figure 8:
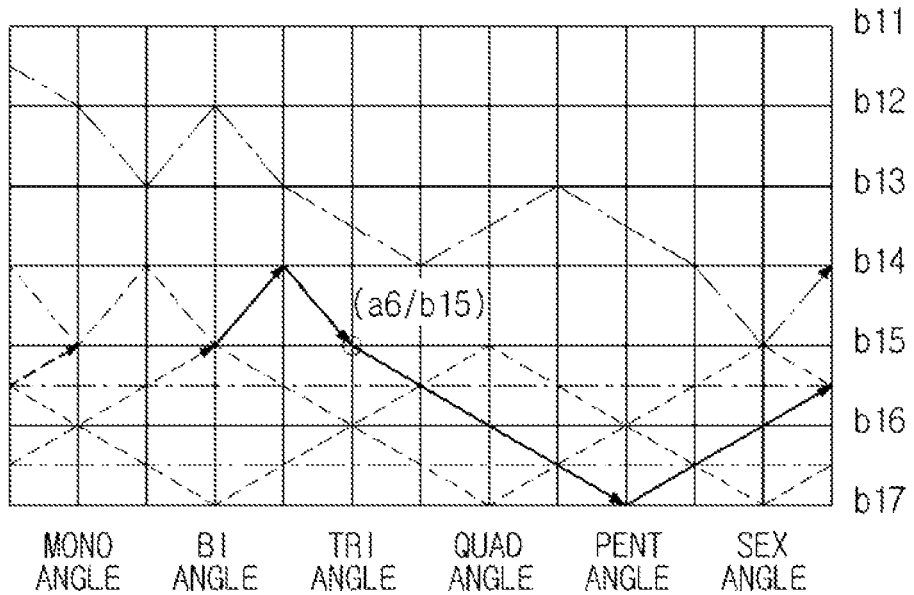
Figure 9:
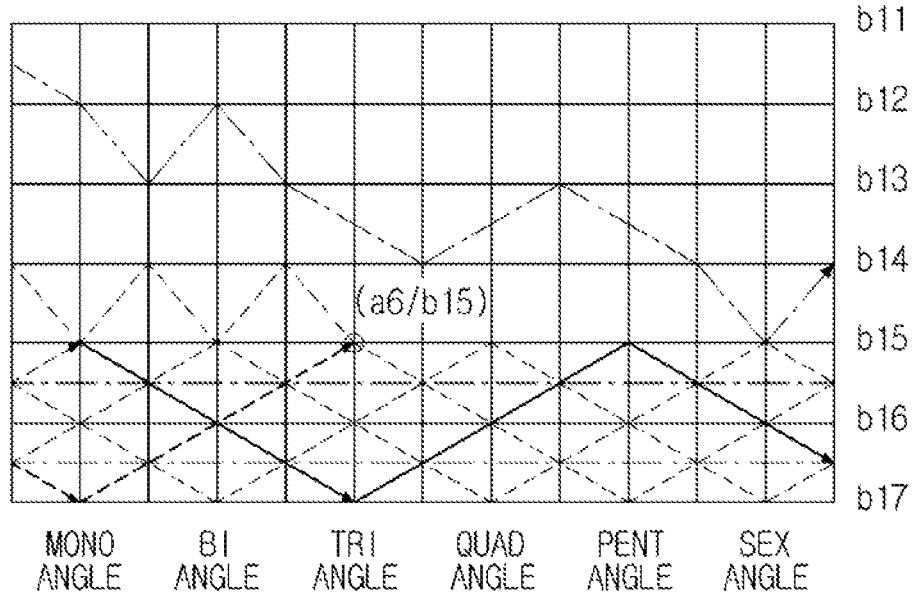

That is, as shown in FIG. 5, the wire 200 starts from this transition point located at the projecting pin 11 of the four-segment diagonal distance (4 l) first, and travels three times the one-segment diagonal distance (1 l) to another projecting pin 11 in the zigzag pattern. Then, the wire travels three times the two-segment diagonal distance to another projecting pin 11 in the zigzag pattern again. This process is the downward wire bending process (cycle). This downward wire bending process is repeated, so that the wire is bent within a predetermined distance in a downward direction, and is located at a transition point a11/b14.

As shown in FIGS. 6 to 9, the wire 200 travels five times the one-segment diagonal distance (1 l) from the transition point a11/b14 located in the downward wire bending process wire to a transition point a4/b15 in a zigzag pattern at an acute angle again, and then travels six times the four-segment diagonal distance (4 l) from the transition point a4/b15 to the same transition point a4/b15 in a zigzag pattern. Thereby, three triangular bending finishing ends 210 are formed. To form the remaining triangular bending finishing ends 210, the wire travels two times the one-segment diagonal distance (1 l) from the transition point a4/b15 to a transition point a6/b15 in a zigzag pattern at an acute angle, and then travels six times the four-segment diagonal distance (4 l) from the transition point a6/b15 to the same transition point a6/b15. Thereby, sexangular bending finishing ends 210 are formed. This is the lower head forming process having a rhombic cell C1.

Here, the reason the wire 200 travels five times the one-segment diagonal distance (1 l) from the transition point a11/b14 to the transition point a4/b15 in the zigzag pattern again is to, because a route along which the wire 200 is overlapped in order to form the first triangular bending finishing ends 210 is not formed, form the route along which the triangular wire is overlapped to thereby carry out a bending traveling process.

Further, the reason the wire travels two times the one-segment diagonal distance (1 l) from the transition point a4/b15 to the transition point a6/b15 in the zigzag pattern at the acute angle is to form the route along which the wire 200 is overlapped in order to form the remaining triangular bending finishing ends 210 to thereby carry out the bending traveling process.

Figure 10:
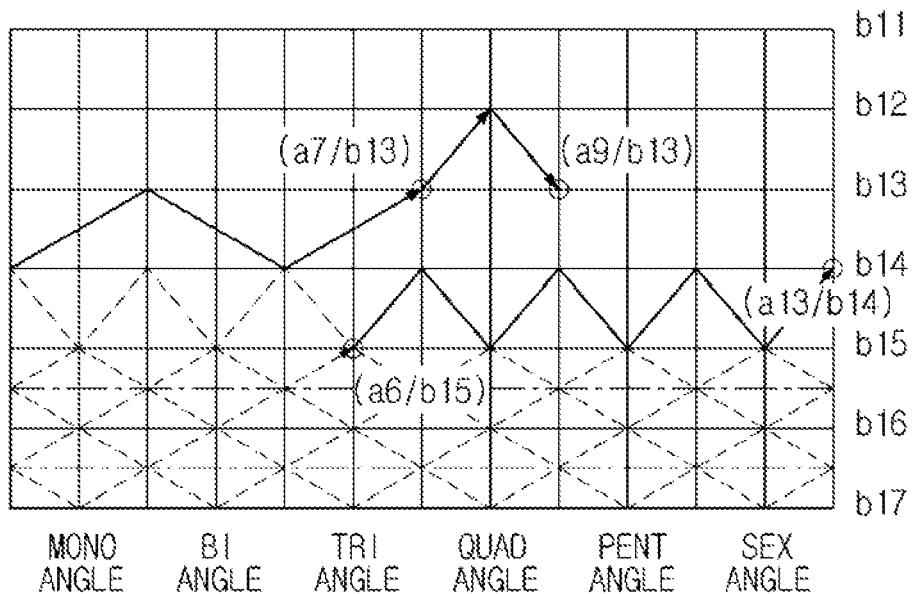
FIGS. 10 to 13 are development views for describing an upward wire bending process of the present invention.
Figure 11:
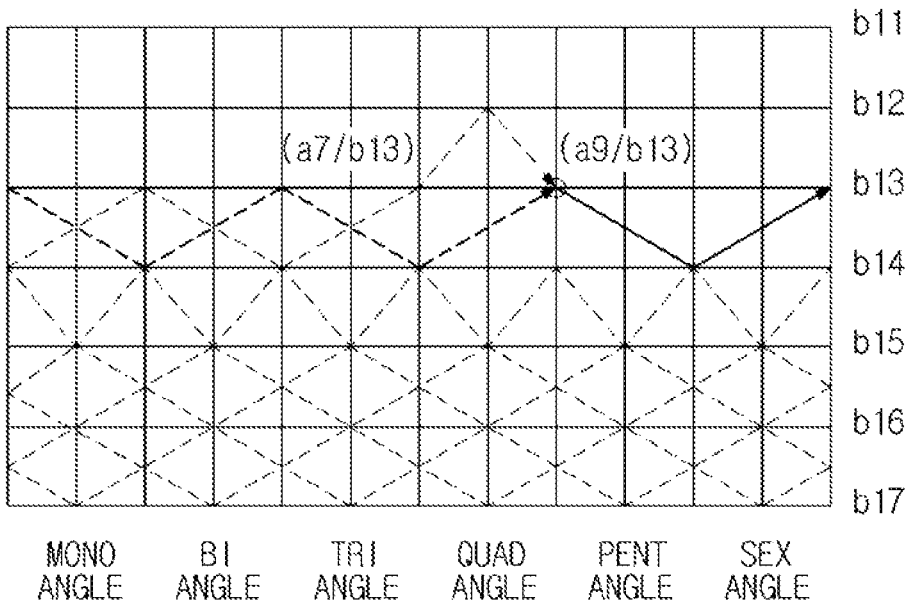

As shown in FIG. 10, the wire 200 travels seven times the one-segment diagonal distance (1 l) from the transition point a6/b15 located in the lower head forming process to a transition point a13/b14 in a zigzag pattern at an acute angle again, travels three times the two-segment diagonal distance (2 l) from the transition point a13/b14 to a transition point a7/b13 in a zigzag pattern at an obtuse angle, and travels two times the one-segment diagonal distance (1 l) from the transition point a7/b13 to a transition point a9/b13 in a zigzag pattern at an acute angle. As shown in FIG. 11, the wire travels six times the two-segment diagonal distance (2 l) from the transition point a9/b13 to a transition point a9/b13 in a zigzag pattern at an obtuse angle.

Figure 12:
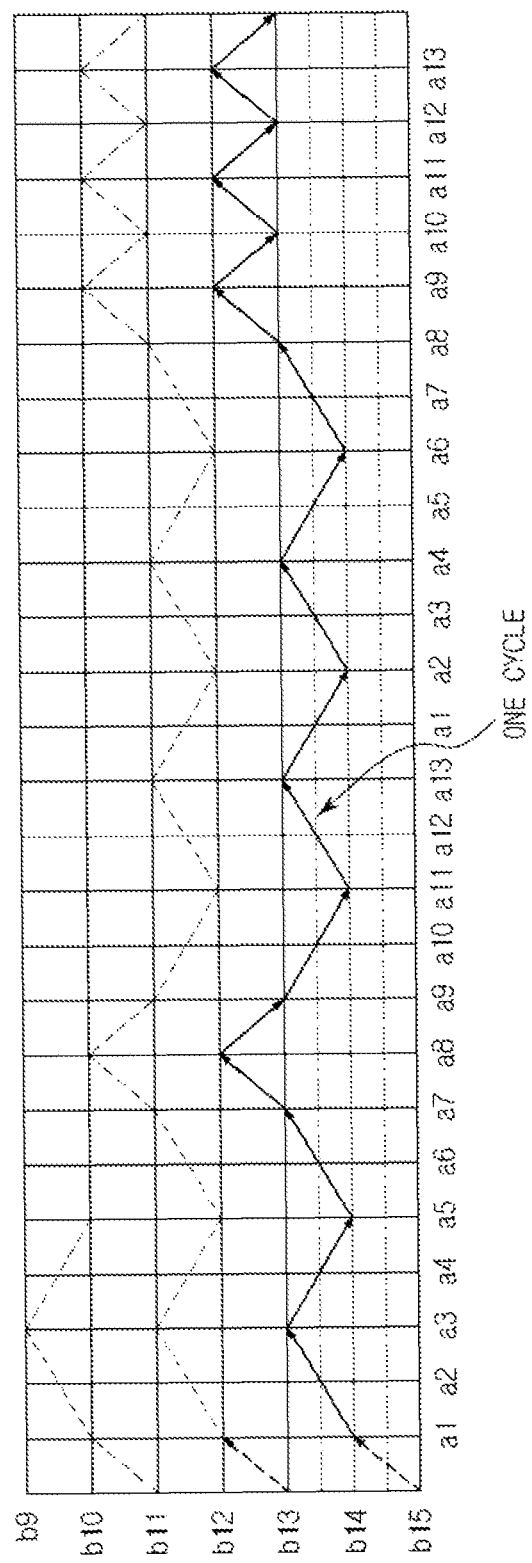
Figure 13:
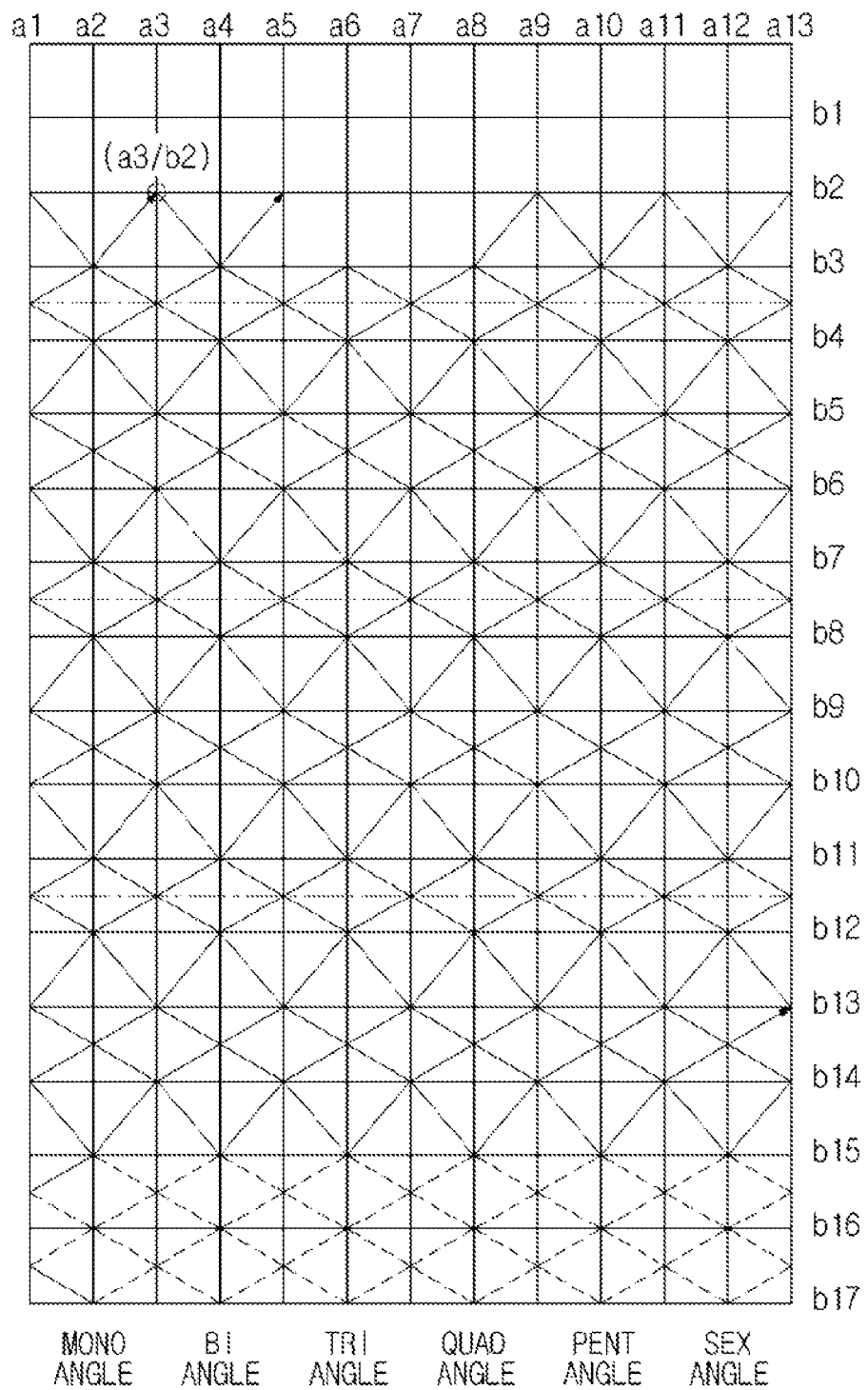
Figure 14:
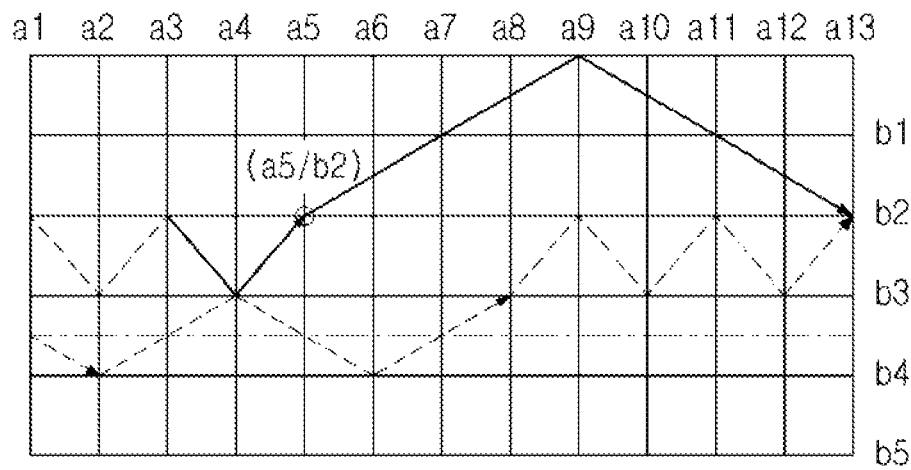
FIGS. 14 to 18 are development views for describing an upper head forming process of the present invention.

In detail, as shown in FIG. 12, the wire travels seven times the one-segment diagonal distance (1 l) from the transition point located in the lower head forming process to the projecting pin 11 in the zigzag pattern, travels three times the two-segment diagonal distance (2 l) to the projecting pin 11 in the zigzag pattern again, travels two times the one-segment diagonal distance (1 l) to the projecting pin 11 in the zigzag pattern again, and travels six times the two-segment diagonal distance (2 l) to the projecting pin 11 in the zigzag pattern again. This is the upward wire bending process (cycle). This upward wire bending process is repeated, so that the wire 200 is bent within a predetermined distance in an upward direction, and is located at a transition point a3/b2.

In the upward wire bending process of sequentially bending the wire 200, the wire is joined crosswise at the transition point (bending vertex) overlapped with the transition point (bending vertex) of the downward wire bending process, and is bent in an upward direction. Thereby, a starry cell C2 is repetitively formed.

Figure 15:
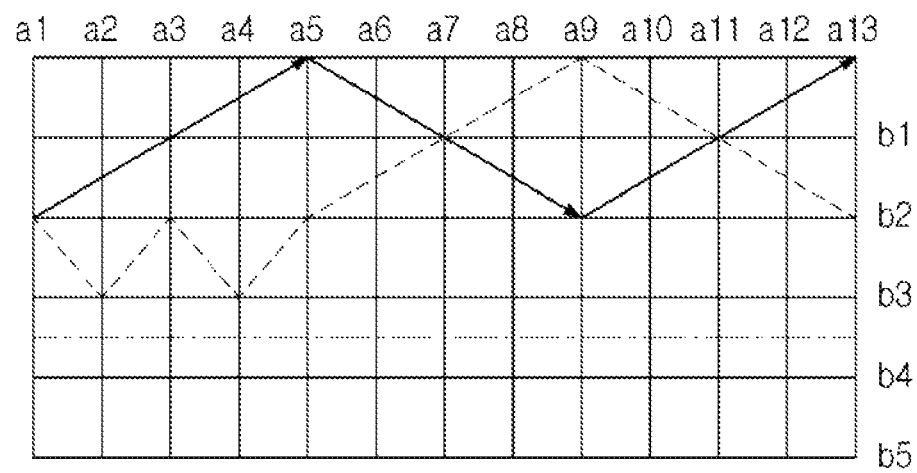
Figure 16:
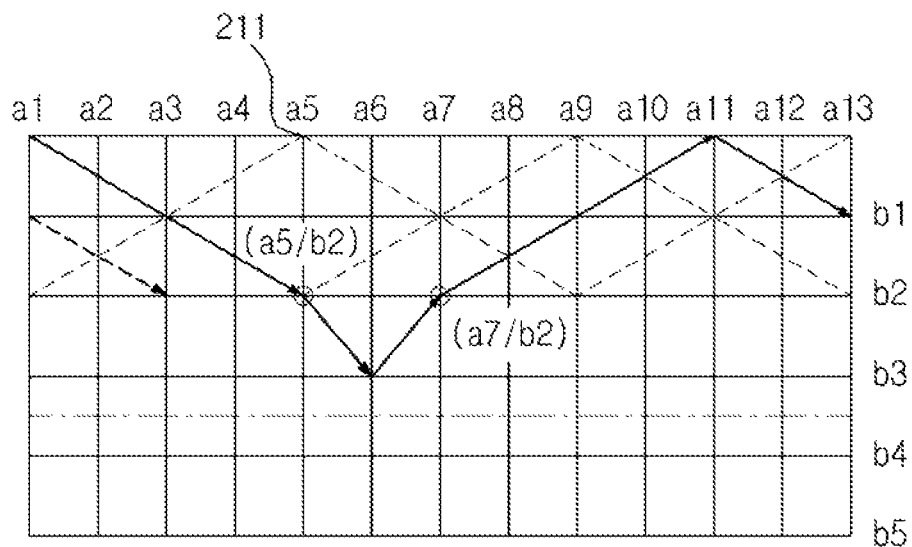
Figure 17:
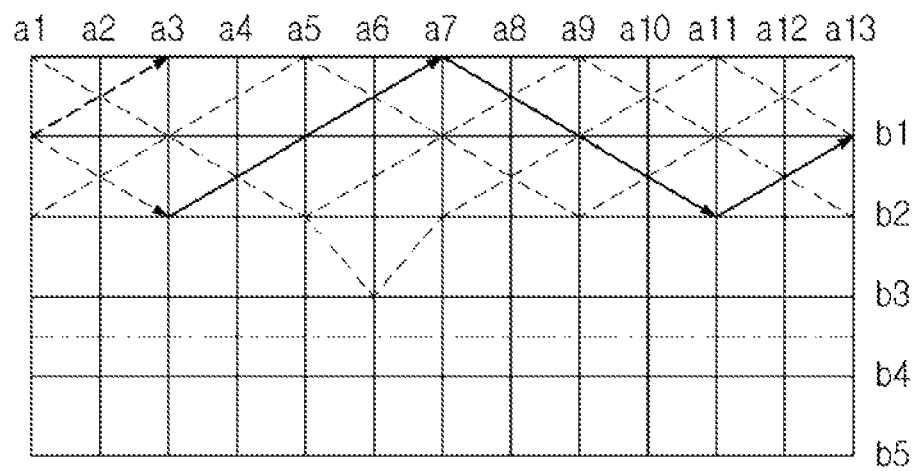

As shown in FIGS. 14 to 17, the wire 200 travels two times the one-segment diagonal distance (1 l) from the transition point a3/b2 located in the upward wire bending process to a transition point a5/b2 in a zigzag pattern at an acute angle again (see FIG. 14), and travels six times the four-segment diagonal distance (4 l) from the transition point a5/b2 to a transition point a5/b2 in a zigzag pattern, thereby forming three triangular bending finishing ends 211 (see FIGS. 15 and 16). To form the remaining triangular bending finishing ends 211, the wire 200 travels two times the one-segment diagonal distance (1 l) from the transition point a5/b2 to a transition point a7/b2 in a zigzag pattern at an acute angle, and then travels six times the four-segment diagonal distance (4 l) from the transition point a7/b2 to the same transition point a7/b2.

Thereby, sexangular bending finishing ends 211 are formed. This is the upper head forming process having a rhombic cell C1 (see FIG. 17).

In the upper head forming process, the reason the wire 200 travels two times the one-segment diagonal distance (1 1) from the transition point a3/b2 to the transition point a5/b2 in the zigzag pattern at the acute angle again is to, because a route along which the wire 200 is overlapped in order to form the first triangular bending finishing ends 211 is not formed, form the route along which the triangular wire is overlapped to thereby carry out a bending traveling process.

Further, the reason the wire travels two times the one-segment diagonal distance (1 1) from the transition point a2/b2 to the transition point a7/b2 in the zigzag pattern at the acute angle is to form the route along which the wire 200 is overlapped in order to form the remaining triangular bending finishing ends 211 to thereby carry out the bending traveling process.

Figure 18:
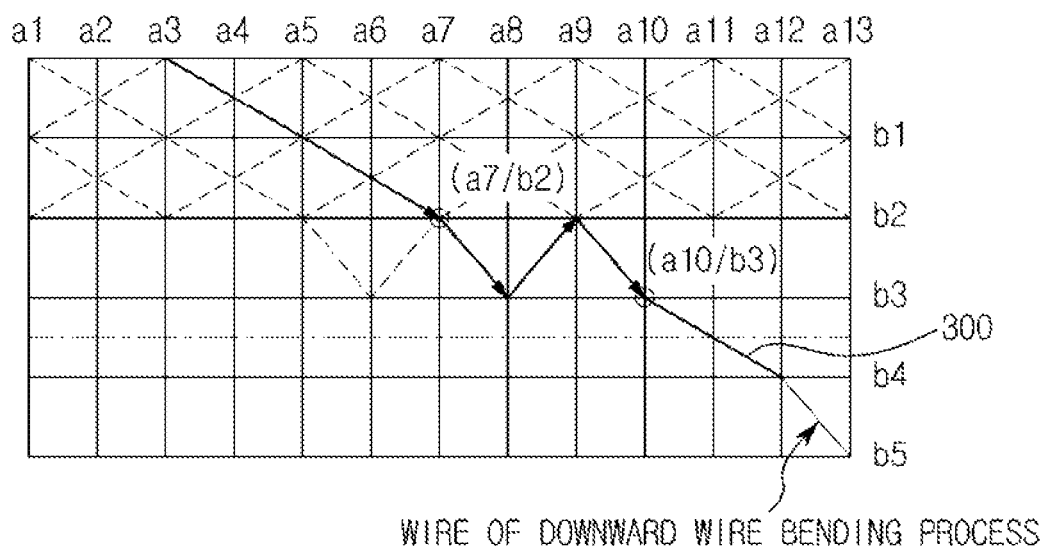
Figure 19:
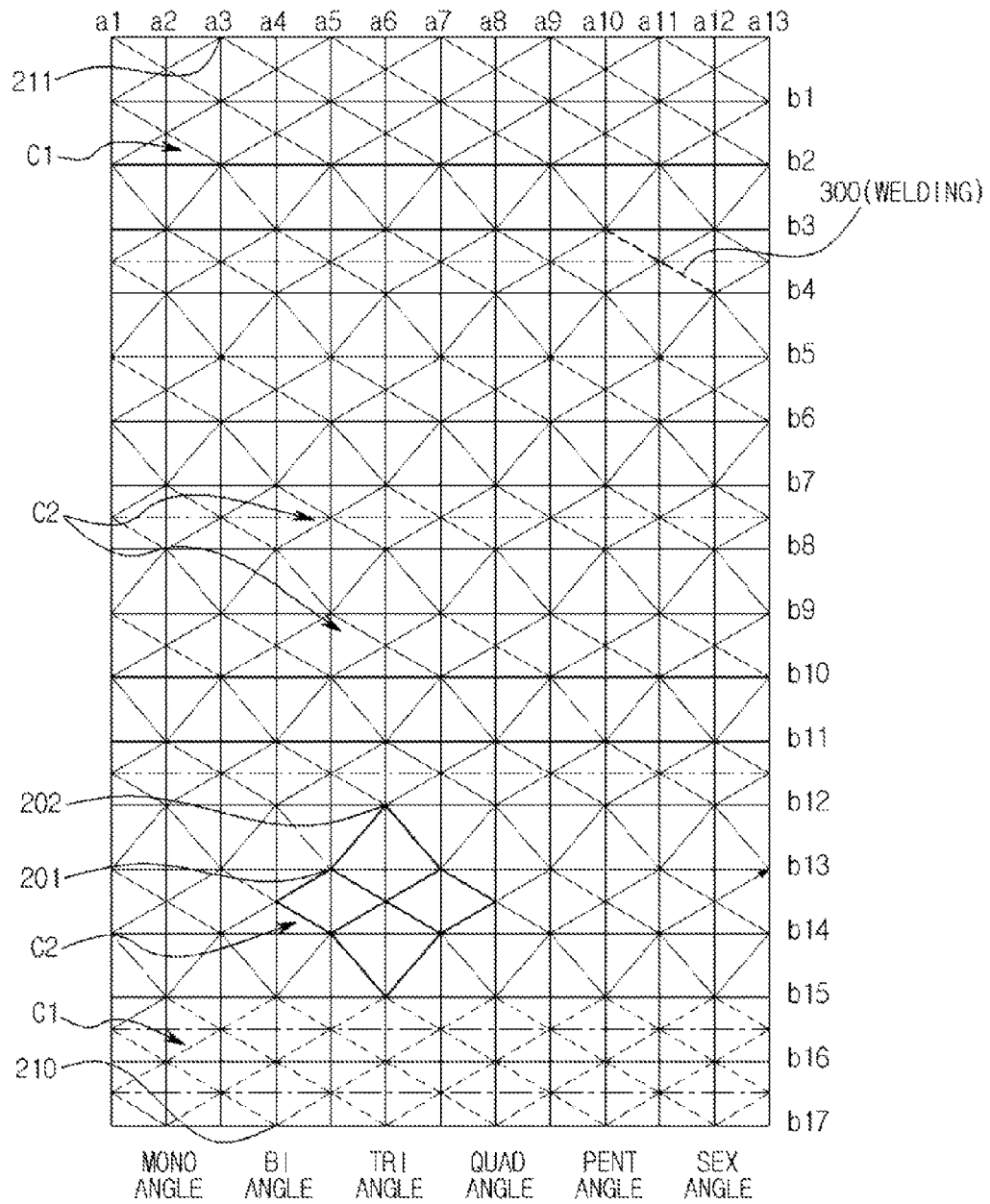
FIG. 19 is a development view showing an entire wire of a crossed and bent state of the present invention.

As shown in FIG. 18, the wire 200 travels three times the one-segment diagonal distance (1 1) from the transition point a7/b2 located in the upper head forming process to a transition point (projecting pin) a10/b3 in a zigzag pattern at an acute angle, and travels the two-segment diagonal distance (2 1) from the transition point a10/b3 at an obtuse angle. The wire 200 is coupled with the wire 200 bent in the downward wire bending process at an overlapped portion by welding 300. Thereby, the finishing connecting process is completed.

Here, the remainders of the start end and the terminal end of the wire 200 excluding the welded portion are cut. In this state, the projecting pins 11 are separated from the basic jig 10, and then a cylindrical body is separated and undergoes heat treatment. Thereby, the stent 100 having a middle body in which the starry cells C2 are formed in the middle thereof as shown in FIG. 10 and upper and lower heads in which the rhombic cells C1 are formed at upper and lower portions thereof and which have the sexangular bending finishing ends is manufactured as shown in FIG. 20.

To perform the heat treatment on the stent 100 manufactured in the manufacturing method of the present invention, a process of forming the hollow cylindrical body and then memorizing its shape at such a temperature as to avoid losing elasticity of the wire 200 is used. This heat treatment technique is disclosed in detail in the prior application of the present applicant, and so detailed description thereof will be omitted.

Figure 20:
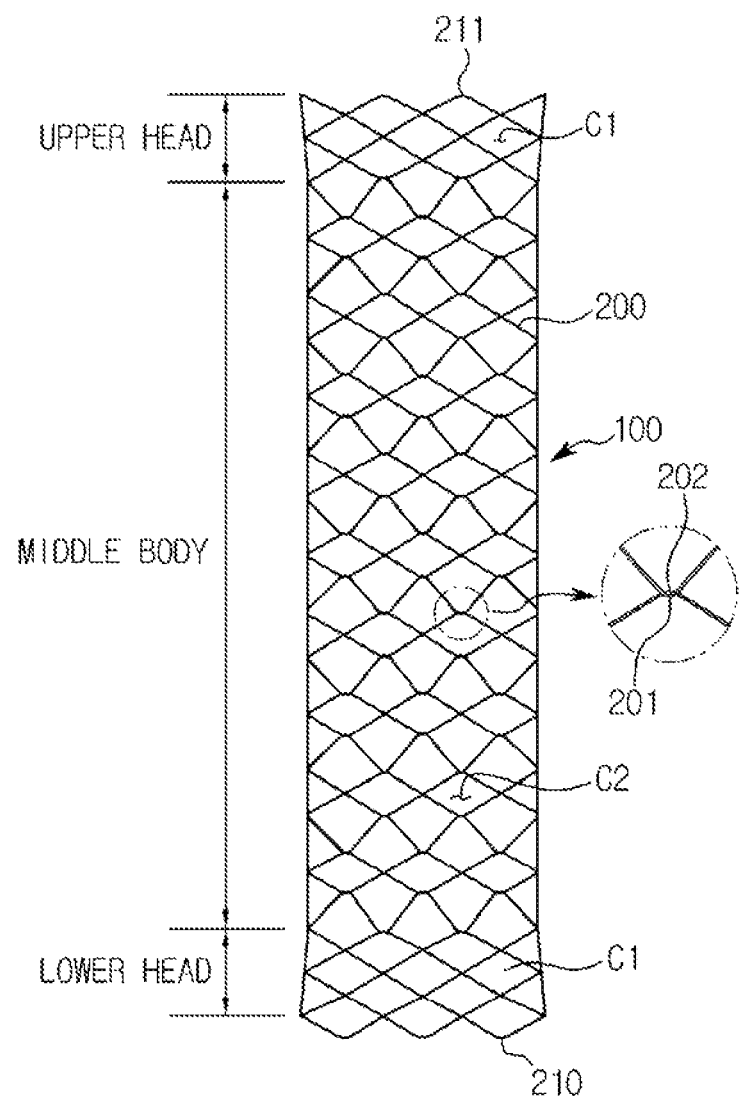
FIG. 20 is a front view of a stent manufactured by a manufacturing method of the present invention.

As shown in FIG. 20, the stent 100 manufactured in the manufacturing method of the present invention has a structure in which the cells formed by the crossed wire 200 are repetitively formed as the starry cells C2 by joining acute angle bending vertexes 201 bent at an acute angle and obtuse angle bending vertexes 202 bent at an obtuse angle in a crosswise shape and joining the obtuse angle bending vertexes 202 bent at the obtuse angle and the acute angle bending vertexes 201 bent at the acute angle and in the crosswise shape.

Figure 21:
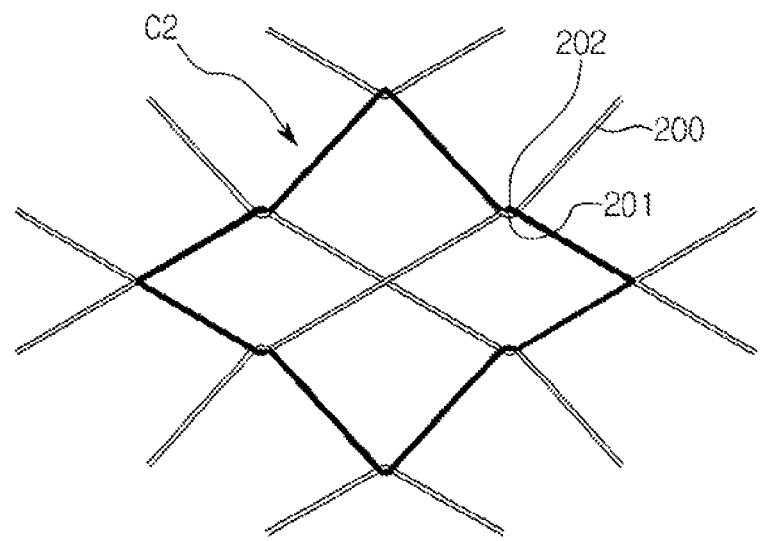
FIG. 21 is a sampled enlarged view of FIG. 20.

In other words, the wires 200 are woven in such a manner that the acute angle bending vertexes 201 and the obtuse angle bending vertexes 202, which are bent downward at the acute angle of the one-segment diagonal distance (1 1) and at the obtuse angle of the two-segment diagonal distance (2 1) in a predetermined cycle in the downward wire bending process, and the obtuse angle bending vertexes 202 and the acute angle bending vertexes 201 of the wire 200, which are bent upward at the obtuse angle of the two-segment diagonal distance (2 1) and at the acute angle of the one-segment diagonal distance (1 1) in a predetermined cycle in the upward wire bending process, are joined crosswise. Thereby, the starry cells C2 are repetitively formed as shown in FIG. 21.

Here, the wires 200 are bent and crossed at an acute angle in the starry cells C2 in a simple crossed structure, and are rapidly displaced when expansion/contraction between the acute angle bending vertexes 201 and the obtuse angle bending vertexes 202 joined crosswise take place in the event of longitudinal expansion or bending. Thus, a flexible bending characteristic is provided.

Figure 22:
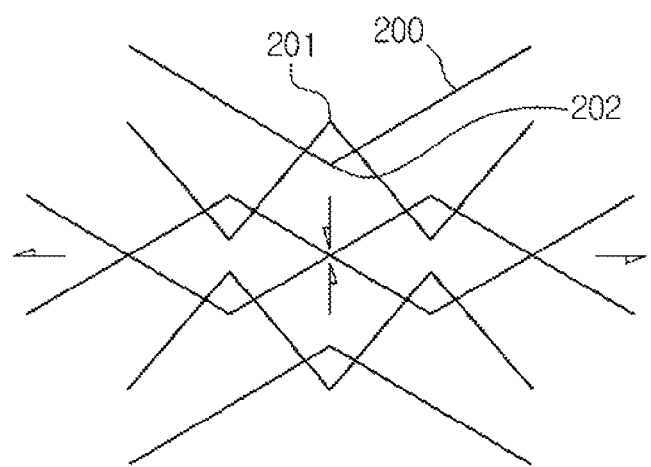
FIGS. 22 to 24 show movement of the wire which is caused by expansion/contraction and bending of the stent of the present invention.
Figure 23:
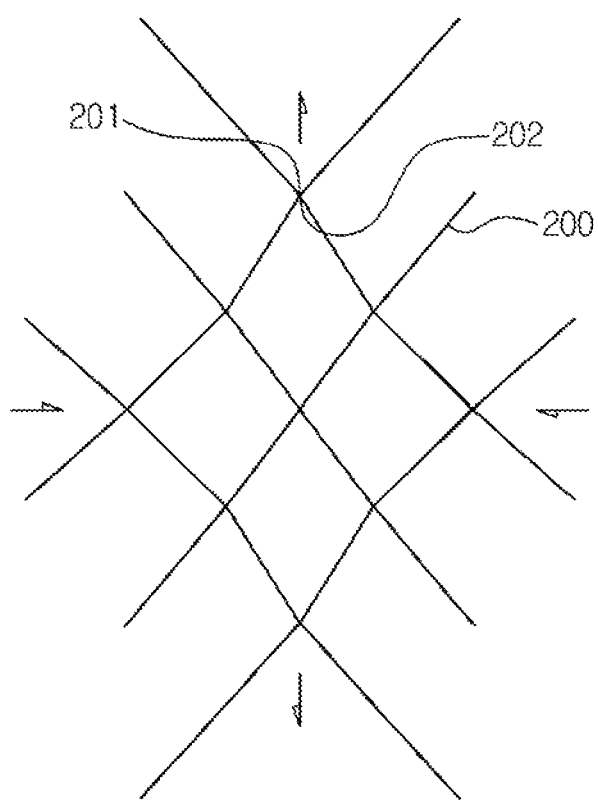
Figure 24:
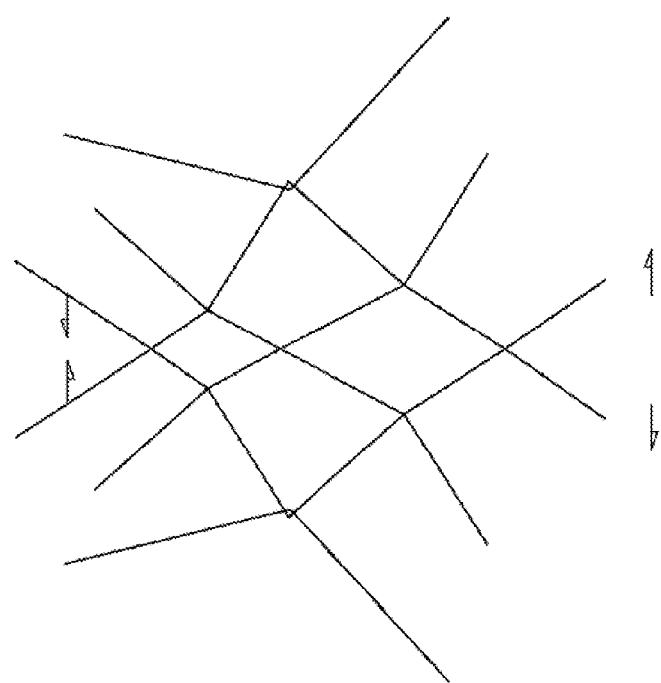

As shown in FIGS. 22 and 23, the expansion/contraction of the stent 100 manufactured in the manufacturing method of the present invention is provided, because the crossed wires 200 are pulled or pushed in such a manner that a distance between each acute angle bending vertex 201 and each obtuse angle bending vertex 202 of the wire 200 is increase or reduced.

As shown in FIG. 22, the acute angle bending vertexes 201 and the obtuse angle bending vertexes 202 are contracted in a bending direction, and are pulled in a crossed state in the opposite direction. Thereby, flexible bending movement is provided.

In other words, the acute angle bending vertexes 201 at which the crossing of the wires 200 forming the starry cells C2 is bent and formed at an acute angle and the obtuse angle bending vertexes 202 at which the crossing of the wires 200 forming the starry cells C2 is bent and formed at an obtuse angle are joined crosswise, and the wires 200 bent at the obtuse angle are joined crosswise and displaced and supported when the expansion/contraction or the bending takes place. Despite severe bending movement, the wires provide flexible movement without being folded. Thus, after a thin film is coated, the coated thin film is not stripped.

Of course, the upper head and the lower head are formed by the wire 200 in which the rhombic cells C1 are formed in two rows and which is uncomplicatedly crossed, and are not accompanied with great stress, so that they do not exert particular influence on the bending movement or expansion.

Figure 25:
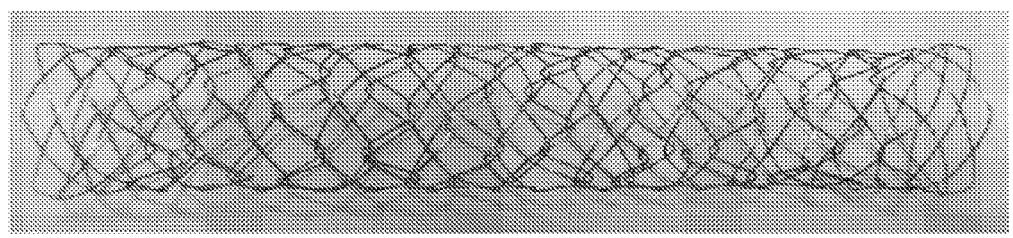
FIG. 25 is a photograph taken of an actual stent manufactured by the present invention.
Figure 26:
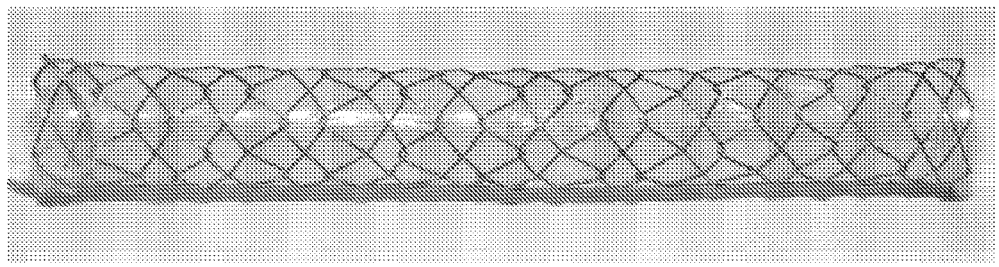
FIG. 26 is a photograph taken of a coated actual stent manufactured by the present invention.
Figure 27:
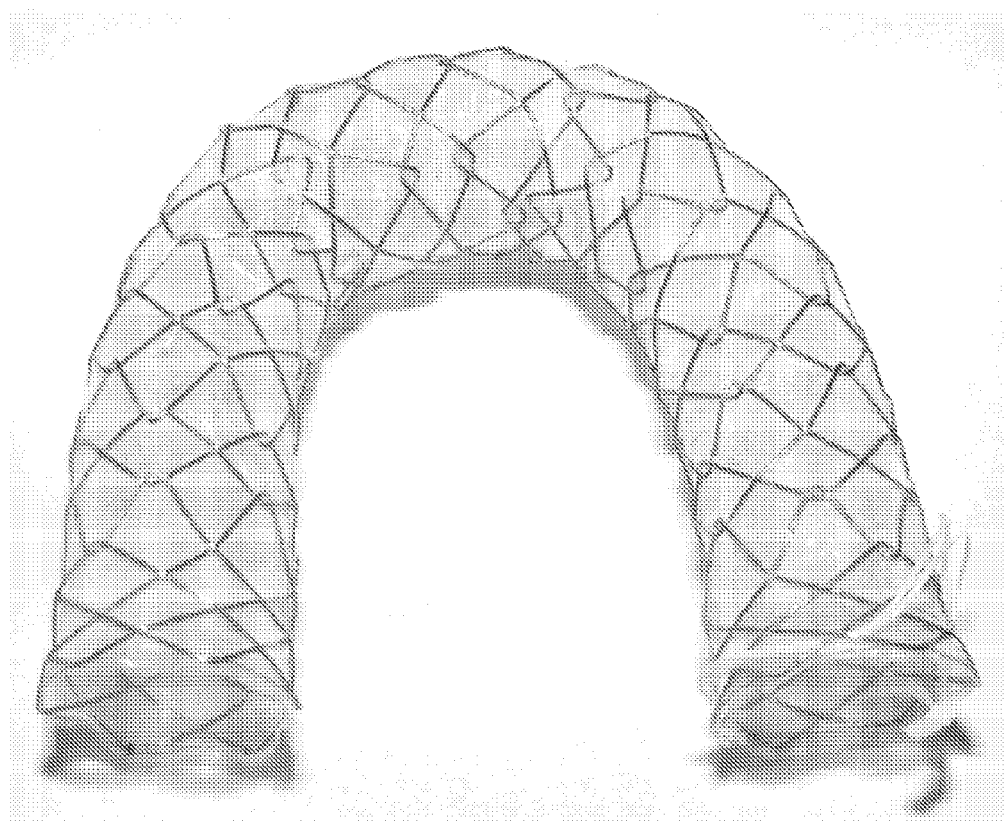
FIG. 27 is a photograph taken of the actual stent of FIG. 26 in a bent state.

An actual stent manufactured by the present invention is shown in FIG. 25 through a photograph. FIG. 26 is a photograph taken of a coated actual stent manufactured by the present invention. FIG. 27 is a photograph showing the actual stent of FIG. 26 in order to show that the real thing is not folded even when is bent in a U shape.

That is, in a state in which an inner and/or outer surface of the stent of the present invention is coated with a coating material such as silicone or polytetrafluoroethylene (PTFE) as in a typical method, the stent is bent in the U shape, and is not folded. Thus, it can be found that the bending characteristic of the stent is very good.

This coating material is used to prevent lesion cells from penetrating into a lumen after the stent is inserted into the lumen.

The invention claimed is:

1. A stent having bending characteristics comprising:
an upper head including a plurality of rhombic cells;
a lower head including a plurality of rhombic cells; and
a middle body including a plurality of starry cells,
wherein each of the plurality of rhombic cells are formed by crossed wires, and
wherein each of the plurality of starry cells are formed by wires having acute angle bending vertexes bent at an acute angle, and obtuse angle bending vertexes bent at an obtuse angle, such that the acute bending vertexes and the obtuse bending, vertexes are joined crosswise between the upper and lower heads, and the obtuse angle bending vertexes bent at the obtuse angle and the acute angle bending vertexes bent at the acute angle are crossed to form repetitive starry cells having a flexible bending characteristic thereby preventing the stent from folding even when the stent is bent sharply.

2. The stent according to claim 1, wherein the repetitive starry cells are smoothly bent in such a way that the wires bent at the acute and obtuse angle by the acute and obtuse angle bending vertexes joined crosswise are crossed when expanded/contracted or bent in a lengthwise direction, and the repetitive starry cells are expanded or contracted by widening or narrowing the acute and obtuse angle bending vertexes in a crossed state by rapid movement of the crossed wires such that the acute and obtuse angle bending vertexes of a bent direction are contracted and the acute and obtuse angle bending vertexes of an opposite direction of the bent direction are pulled in the crossed state.

3. The stent according to claim 1, wherein the rhombic cells of the upper and lower heads are formed in two rows by the crossed wires.

4. The stent according to claim 1, wherein the stent is coated with a coating material on an inner or outer side thereof.

* * * * *